United States Patent
Kang et al.

[11] Patent Number: 5,980,917
[45] Date of Patent: Nov. 9, 1999

[54] OIL-IN-WATER TYPE COSMETIC COMPOSITION CONTAINING RETINOIDS STABILIZED BY A LIQUIDCRYSTAL

[75] Inventors: Hak Hee Kang, Seongnam; Jun Chul Cho, Seoul; Jung Su Kim, Suwon; Ok Sob Lee, Anyang, all of Rep. of Korea

[73] Assignee: Pacific Corporation, Seoul, Rep. of Korea

[21] Appl. No.: 08/956,291

[22] Filed: Oct. 23, 1997

[30] Foreign Application Priority Data

Sep. 12, 1997 [KR] Rep. of Korea ............ 97-47231

[51] Int. Cl.⁶ ............................................. A61K 7/00
[52] U.S. Cl. ................... 424/401; 514/725; 514/938
[58] Field of Search ............... 424/401; 514/725, 514/938

[56] References Cited

U.S. PATENT DOCUMENTS

| | | | |
|---|---|---|---|
| 4,247,547 | 1/1981 | Marks | 424/240 |
| 4,466,805 | 8/1984 | Welters et al. | 8/406 |
| 4,603,146 | 7/1986 | Kligman | 514/559 |
| 4,826,828 | 5/1989 | Wilmott et al. | 514/63 |
| 4,877,805 | 10/1989 | Kligman | 514/381 |
| 5,658,575 | 8/1997 | Ribier et al. | 424/401 |

*Primary Examiner*—S. Mark Clardy
*Assistant Examiner*—Michael A. Williamson
*Attorney, Agent, or Firm*—Foley & Lardner

[57] ABSTRACT

Disclosed herein is an oil-in-water type cosmetic composition containing retinoids stabilized within a core of a liquidcrystal formed by a surfactant having a phase transition temperature of 45° C. or higher and a bulky structure.

6 Claims, 1 Drawing Sheet

OIL-IN-WATER TYPE COSMETIC COMPOSITION CONTAINING RETINOIDS STABILIZED BY A LIQUIDCRYSTAL

BACKGROUND OF THE INVENTION

1. Field of the Invention

The present invention relates to an oil-in-water type cosmetic composition containing retinoids. More particularly it relates to an oil-in-water type cosmetic composition containing retinoids stabilized within a core of a liquidcrystal formed by a surfactant having a high phase transition temperature and a bulky structure.

2. Description of Related Art

In a cosmetic field, there have been many studies for development of new material which can promote cell differentiation and regeneration, and can increase collagen biosynthesis, and is safe to the skin. As a material satisfying these needs, vitamins have been concentrated on and utilized as a cosmetic ingredient. Among these vitamins, retinoids are very effective in improving a skin state, and therefore many concerns have been concentrated on these retinoids.

It is known that retinoids are very effective in recovering the skin from various damages caused by wrinkles, roughness, drying or abnormal peeling(U.S. Pat. No. 4,603, 146 and U.S. Pat. No. 4,877,805). Retinoids include retinol, retinal, retinyl palmitate, retinyl acetate, retinoic acid and the like. Among them, in consideration of efficacy and safety to the skin, retinol is the most compatible for the skin.

Retinol and its derivatives have an outstanding effect in preventing the formation of skin wrinkles. However, they are easily oxidized in an air or in an aqueous solution, and loss their stability and physiological activities. Due to their instability, there has been a limit in incorporating retinol into cosmetic formulations.

Under this circumstance, many studies have been conducted to stabilize retinol in a cosmetic composition. In particular, there has been proposed an oil-in-water type(O/W type) emulsion wherein retinol is stabilized by an antioxidant such as BHT(butylated hydroxytoluene), BHA (butylated hydroxyanisole), tocopherol and its derivatives, ascorbic acid(vitamin C) and citric acid. For examples, U.S. Pat. No. 4,466,805 discloses an O/W type cosmetic composition containing retinol stabilized by an antioxidant such as BHT and dl-α-tocopherol and a chelating reagent such as EDTA(ethylenediaminetetraacetic acid). And, U.S. Pat. No. 4,247,547 discloses a gel-type cosmetic composition containing retiol stabilized by an antioxidant such as BHT, BHA, ascorbic acid, propyl gallate and α-tocopherol.

However, although retinoids can be stabilized to some extent by these antioxidants, excessive use of antioxidant may cause skin irritation. And, there is a limit in stabilizing retinoids without blocking contact with water which is present in a cosmetic base. Further, since instability of retinoids may be accelerated by oxygen attack through the medium of aqueous solution, many research for stabilization of retinoids are being conducted in a structural aspect of emulsion system itself.

On the other hand, in water-in-oil type(W/O type) emulsion, since water of a core is surrounded with outer oily film and oxygen supply from outer atmosphere is blocked, retinoids can be more stabilized than in an O/W type emulsion. Further, U.S. Pat. No. 4,826,828 discloses a W/O type emulsion containing retinoids together with a fat-soluble antioxidant such as BHT and BHA. However, W/O type emulsion tends to be oily and greasy, resulting in a poor feel of cosmetics. Additionally, it is difficult to stabilize an emulsion itself Accordingly, the present inventors have conducted extensive studies in order to stabilize retinoids in an O/W type emulsion rendering good feel to the skin.

In order to stabilize retinoids, above all, a contact with air or water has to be blocked to a minimum as possible. Accordingly, the present inventors made efforts to find a method for blocking retinoids in a core from being in contact with water in an outer and for minimizing the transfer of components between these compartments.

In general, a combination of surfactants, fatty alcohols and polyols forms liquidcrystals. However, since this liquidcrystal has flexibility and permeability, material transfer between a core and an outer may occur through liquidcrystal film, and thereby it is difficult to stabilize retinoids of a core. The present inventors found that use of surfactants having a high phase transition temperature and a bulky structure forms a strip-shape, wide and dense liquidcrystal film and thereby material transfer between a core and an outer can be remarkably reduced. They guessed active ingredients of a core to be trapped and fixed within a lamella structure of a thick and dense liquidcrystal film. The present invention was accomplished based on this finding.

SUMMARY OF THE INVENTION

Thus, an object of this invention is to provide a method for stabilizing retinoids in an O/W type cosmetic composition.

Another object of this invention is to provide an O/W type cosmetic composition containing retinoids without appreciable loss of its activity.

Still another object of this invention is to provide a method for preparing said O/W type cosmetic composition.

The above and other objects and features of the present invention will be apparent to the skilled in the art from the following detailed description.

DETAILED DESCRIPTION OF THE INVENTION

Figure 1:
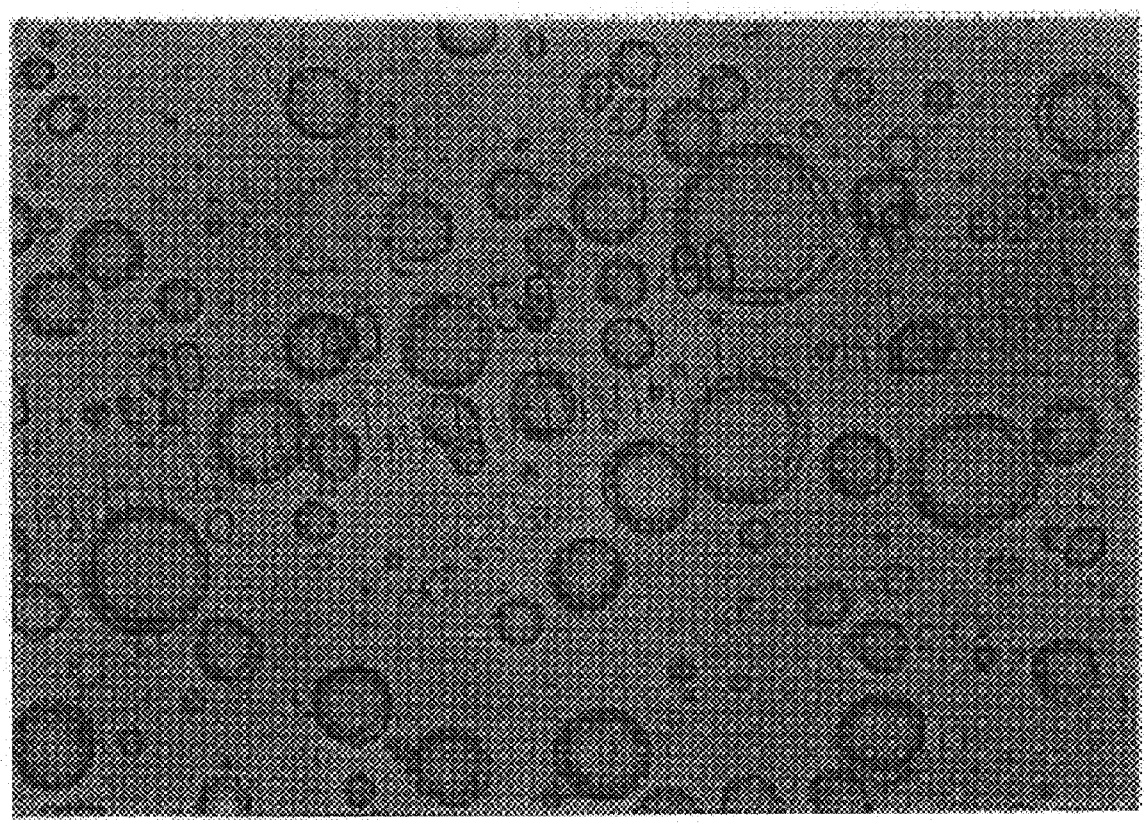
FIG. 1 is a photograph showing the formation of SWLC in Example 1.

In order to accomplish the above objects, the present invention provides an oil-in-water type(O/W type) cosmetic composition wherein retinoid as an active ingredient is contained within a core of a liquidcrystal formed by a combination of 0.5~20% by weight of a surfactant having a phase transition temperature of 45° C. or higher, 0.1~10% by weight of fatty alcohol and 0.1~10% by weight of cholesterol, based on a total weight of the composition.

Further, the present invention provides an O/W type cosmetic composition containing one or more retinoids selected from a group consisting of retinol, retinal, retinoic acid and its esters, in an amount of 100~50,000 IU per 1 g of composition.

The O/W type cosmetic composition according to the present invention will be described in more detail.

The present invention is provided for stabilizing retinoids in an O/W type cosmetics, and is characterized in that it contains a surfactant having a phase transition temperature of 45° C. or higher as a liquidcrystal-forming material, together with fatty alcohol and cholesterol. Examples of this surfactant may include, but not limited thereto, polyglyceryl (n=2~12) monostearate, polyglyceryl(n=2~12) distearate, polyglyceryl(n=2~12) tristearate, polyglyceryl(n=2~12) tetrastearate, polyglyceryl(n=2~12) pentastearate, polyglyceryl(n=2~12) monopalmitate, polyglyceryl(n=2~12) dipalmitate, polyglyceryl(n=2~12) tripalmitate, polyglyceryl(n=2~12) tetrapalmitate, polyglyceryl(n=2~12) pentapalmitate, stearyl polyglucose, cetearyl polyglucose, polyglyceryl(n=2~12) alkylglucose monostearate, polyglyceryl(n=2~12) alkylglucose distearate, polyglyceryl (n=2~12) alkylglucose tristearate, polyglyceryl(n=2~12) alkylglucose tetrastearate, polyglyceryl(n=2~12) alkylglucose pentastearate, polyglyceryl(n=2~12) alkylglucose monopalmitate, polyglyceryl(n=2~12) alkylglucose dipalmitate, polyglyceryl(n=2~12) alkylglucose tripalmitate, polyglyceryl(n=2~12) alkylglucose tetrapalmitate, and polyglyceryl(n=2~12) alkylglucose pentapalmitate. The surfactant may be employed alone or in combination with one or more other surfactants. Specific examples are NIKKOMULESE-41 (polyglyceryl(10) pentastearate-behenyl alcohol-sodium stearoyl lactoylate) available by Nikko Chemical Co., Ltd., EMULGADE PL-1618 (cetearyl alcohol-cetearyl polyglucose) available by Henkel Co., Ltd., and TEGOCARE 450 (polyglyceryl (3)-methylglucose distearate) available by Goldschmidts Co., Ltd. This surfactant may be employed in an amount of 0.5~20% by weight based on a total weight of the composition.

This surfactant having 45° C. or higher phase transition temperature together with fatty alcohol and cholesterol is present in the form of lamella in small portion of water and forms a thick and dense liquidcrystal film surrounding oily materials. The liquidcrystal film formed in the present invention has a wide and rigid strip-shape as shown in FIG. 1. So, in this application, it is named as SWLC(Super Wide LiquidCrystal).

A method for preparing O/W type cosmetic composition according to the present invention will be described in more detail.

The method according to the present invention comprises following steps:

(1) Preparation of a SWLC base:

A combination of the above-described surfactant, fatty alcohol and cholesterol is mixed and emulsified in small portion of distilled water at a temperature of about 70° C., and then retinoids as a core are added thereto. Then, resulting mixture is cooled to a room temperature to give a SWLC base.

(2) Preparation of a gel-type base:

Aqueous part is emulsified by using the same surfactants as that for forming liquidcrystals, and then is cooled to a room temperature. Then, water-soluble polymer is added thereto to give a gel-type base.

(3) Mixing:

The SWLC base of the step (1) is added to the gel-type base of the step (2), and then mixed to give an O/W type cosmetics.

Since critical or higher concentration of surfactants are present in the gel-type base of the step (2), the surfactants constructing the liquidcrystals can be prevented from sudden releasing into the gel-type base. That is, SWLC surrounding a core containing retinoids maintains compact and dense lamella structure at a room temperature which is lower than the phase transition temperature of the surfactant. This compact lamella structure is expected to block the transfer of components between a core and an outer. As confirmed in the below-described experimental examples, retinoid contained in the cosmetic composition of the present invention has its activity to about 82%, during a storage of 4 weeks, under an environment of 45° C.

And, for further stabilization of retinoids, the composition according to the present invention may contain an antioxidant such as BHT and BHA, and a chelating reagent such as EDTA.

PREFERRED EMBODIMENT OF THE INVENTION

The present invention will be described in more detail by way of the following examples. However, these examples are provided for only illustration purpose and should not be construed as limiting the scope of the invention, which is properly delineated in the accompanying claims.

| | Comparative Examples 1~7 | | | | | | |
|---|---|---|---|---|---|---|---|
| | Comparative Examples | | | | | | |
| Materials | 1 | 2 | 3 | 4 | 5 | 6 | 7 |
| 1. Stearic acid | 1.0 | 1.0 | 1.0 | 1.0 | 1.0 | 1.0 | 1.0 |
| 2. Cetostearyl alcohol | — | — | — | — | 1.5 | — | 1.5 |
| 3. Liquid paraffin | 3.0 | 3.0 | 3.0 | 3.0 | 3.0 | 3.0 | 3.0 |
| 4. Monostearic sorbitan | 0.3 | 0.3 | 0.3 | 0.3 | 0.3 | 0.3 | 0.3 |
| 5. Monostearic polyoxyethylene(20) sorbitan | 3.0 | 3.0 | 3.0 | 3.0 | 3.0 | 3.0 | 3.0 |
| 6. Caprylic/capric triglyceride | 5.0 | 5.0 | 5.0 | 5.0 | 5.0 | 5.0 | 5.0 |
| *7. NIKKOMULESE-41 | — | — | — | — | — | — | — |
| *8. EMULGADE PL-1618 | — | — | — | — | — | — | — |
| *9. TEGOCARE 450 | — | — | — | — | — | — | — |

-continued

Comparative Examples 1~7

| Materials | Comparative Examples | | | | | | |
|---|---|---|---|---|---|---|---|
| | 1 | 2 | 3 | 4 | 5 | 6 | 7 |
| 10. Cholesterol | — | — | — | — | 0.5 | — | 0.5 |
| 11. Cyclomethicone | 1.5 | 1.5 | 1.5 | 1.5 | 1.5 | 1.5 | 1.5 |
| 12. Preservative | q.s. | q.s. | q.s. | q.s. | q.s. | q.s. | q.s. |
| 13. BHT | — | — | 0.05 | 0.05 | 0.05 | 0.05 | 0.05 |
| 14. BHA | — | — | 0.05 | 0.05 | 0.05 | 0.05 | 0.05 |
| 15. Distilled water | 8.0 | 8.0 | 8.0 | 8.0 | 8.0 | 8.0 | 8.0 |
| 16. Concentrated glycerine | 15.0 | 15.0 | 15.0 | 15.0 | 15.0 | 15.0 | 15.0 |
| 17. NIKKOMULESE-41 | — | — | — | 0.2 | — | 0.2 | 0.2 |
| 18. EMULGADE PL-1618 | — | — | — | 0.8 | — | 0.8 | 0.8 |
| 19. TEGOCARE 450 | — | — | — | 0.1 | — | 0.1 | 0.1 |
| 20. Cetostearyl alcohol | 0.3 | 0.3 | 0.3 | 0.3 | 0.3 | 0.3 | 0.3 |
| 21. EDTA-2Na | — | 0.05 | 0.05 | 0.05 | 0.05 | 0.05 | 0.05 |
| 22. Distilled water | to 100 | to 100 | to 100 | to 100 | to 100 | to 100 | to 100 |
| 23. KOH | q.s. | q.s. | q.s. | q.s. | q.s. | q.s. | q.s. |
| 24. Hyaruronic acid extracts | 0.5 | 0.5 | 0.5 | 0.5 | 0.5 | 0.5 | 0.5 |
| 25. Carboxyvinyl polymer | 0.12 | 0.12 | 0.12 | 0.12 | 0.12 | 0.12 | 0.12 |
| 26. Perfume | q.s. | q.s. | q.s. | q.s. | q.s. | q.s. | q.s. |
| *27. Retinol(10%) | 1.0 | 1.0 | 1.0 | 1.0 | 1.0 | — | — |
| *28. Retinyl palmitate(10%) | — | — | — | — | — | 0.5 | 0.5 |

(Note)
*7. NIKKOMULESE-41 (manufactured by Nikko Chemical Co., Ltd.): Polyglyceryl(10) pentastearate -behenyl alcohol-sodium stearoyl lactoylate
*8. EMULGADE PL-1618 (manufactured by Henkel Co., Ltd.): Cetearyl alcohol-cetearyl polyglucose
*9. TEGOCARE 450 (manufactured by Goldschmidts Co., Ltd.): Polyglyceryl(3)-methylglucose distearate
*27. Retinol(10%): all trans form of retinol 10% solution in caprylic/capric triglyceride
*28. Retinyl palmitate(10%): 10% of retinol palmitate in caprylic/capric triglyceride Examples 1~7

| Materials | Examples | | | | | | |
|---|---|---|---|---|---|---|---|
| | 1 | 2 | 3 | 4 | 5 | 6 | 7 |
| 1. Stearic acid | 1.0 | 1.0 | 1.0 | 1.0 | 1.0 | 1.0 | 1.0 |
| 2. Cetostearyl alcohol | 1.5 | 1.5 | 1.5 | 1.5 | 1.5 | — | 1.5 |
| 3. Liquid paraffin | 3.0 | 3.0 | 3.0 | 3.0 | 3.0 | 3.0 | 3.0 |
| 4. Monostearic sorbitan | 0.3 | 0.3 | 0.3 | 0.3 | 0.3 | 0.3 | 0.3 |
| 5. Monostearic polyoxyethylene(20) sorbitan | 3.0 | 3.0 | 3.0 | 3.0 | 3.0 | 3.0 | 3.0 |
| 6. Caprylic/capric triglyceride | 5.0 | 5.0 | 5.0 | 5.0 | 5.0 | 5.0 | 5.0 |
| *7. NIKKOMULESE-41 | 0.8 | 0.8 | 0.8 | 3.0 | — | — | 1.0 |
| *8. EMULGADE PL-1618 | 3.0 | 3.0 | 3.0 | — | 3.0 | — | 1.0 |
| *9. TEGOCARE 450 | 0.2 | 0.2 | 0.2 | — | — | 3.0 | 1.0 |
| 10. Cholesterol | 0.5 | 0.5 | 0.5 | 0.5 | 0.5 | 0.5 | 0.5 |
| 11. Cyclomethicone | 1.5 | 1.5 | 1.5 | 1.5 | 1.5 | 1.5 | 1.5 |
| 12. Preservative | q.s. | q.s. | q.s. | q.s. | q.s. | q.s. | q.s. |
| 13. BHT | — | 0.05 | 0.05 | 0.05 | 0.05 | 0.05 | 0.05 |
| 14. BHA | — | 0.05 | 0.05 | 0.05 | 0.05 | 0.05 | 0.05 |
| 15. Distilled water | 8.0 | 8.0 | 8.0 | 8.0 | 8.0 | 8.0 | 8.0 |
| 16. Concentrated glycerine | 15.0 | 15.0 | 15.0 | 15.0 | 15.0 | 15.0 | 15.0 |
| 17. NIKKOMULESE-41 | 0.2 | 0.2 | 0.2 | 0.2 | 0.2 | 0.2 | 0.2 |
| 18. EMULGADE PL-1618 | 0.8 | 0.8 | 0.8 | 0.8 | 0.8 | 0.8 | 0.8 |
| 19. TEGOCARE 450 | 0.1 | 0.1 | 0.1 | 0.1 | 0.1 | 0.1 | 0.1 |
| 20. Cetostearyl alcohol | 0.3 | 0.3 | 0.3 | 0.3 | 0.3 | 0.3 | 0.3 |
| 21. EDTA-2Na | — | 0.05 | 0.05 | 0.05 | 0.05 | 0.05 | 0.05 |
| 22. Distilled water | to 100 | to 100 | to 100 | to 100 | to 100 | to 100 | to 100 |
| 23. KOH | q.s. | q.s. | q.s. | q.s. | q.s. | q.s. | q.s. |
| 24. Hyaruronic acid extracts | 0.5 | 0.5 | 0.5 | 0.5 | 0.5 | 0.5 | 0.5 |
| 25. Carboxyvinyl polymer | 0.12 | 0.12 | 0.12 | 0.12 | 0.12 | 0.12 | 0.12 |

-continued

Examples 1~7

| Materials | Examples | | | | | | |
|---|---|---|---|---|---|---|---|
| | 1 | 2 | 3 | 4 | 5 | 6 | 7 |
| 26. Perfume | q.s. | q.s. | q.s. | q.s. | q.s. | q.s. | q.s. |
| *27. Retinol(10%) | 1.0 | 1.0 | — | 1.0 | 1.0 | 1.0 | 1.0 |
| *28. Retinyl palmitate(10%) | — | — | 0.5 | — | — | 0.5 | — |

(Note)
*7. NIKKOMULESE-41 (manufactured by Nikko Chemical Co., Ltd.): Polyglyceryl(10) pentastearate -behenyl alcohol-sodium stearoyl lactoylate
*8. EMULGADE PL-1618 (manufactured by Henkel Co., Ltd.): Cetearyl alcohol-cetearyl polyglucose
*9. TEGOCARE 450 (manufactured by Goldschmidts Co., Ltd.): Polyglyceryl(3)-methylglucose distearate
*27. Retinol(10%): all trans form of retinol 10% solution in caprylic/capric triglyceride
*28. Retinyl palmitate(10%): 10% of retinol palmitate in caprylic/capric triglyceride

[Preparation]

(1) Materials 1~14 and materials 15~16 were separately mixed and heated up to 70° C. Two mixtures were mixed together and then emulsified under a stirring at 3,600 rpm for 3 minutes. After addition of materials 27 and 28, resulting mixture was cooled to a room temperature, to give a SWLC base. Retinol content contained in these compositions corresponds to 3100 IU per 1 g of composition, and retinyl pamitate content corresponds to 1300 IU per 1 g of composition.

(2) Materials 17~20 and materials 21~23, each was heated to 70° C., and then were mixed and emulsified. After subsequent additions of material 26 and materials 24~25, resulting mixture was cooled to a room temperature, to give a gel-type base.

(3) At a room temperature, the SWLC base of the step (1) was added to the gel-type base of the step (2), and then stirred to give an O/W type composition.

EXPERIMENTAL EXAMPLE 1

Activity of retinol

In order to evaluate stability of retinol in the O/W type composition, the activities of retinols contained in the compositions prepared in Examples and Comparative Examples were measured with HPLC(5 μm, $C_8$ column(25 cm of length×4.6 mm of diameter), ethanol extraction). The results are shown in Table 1.

TABLE 1

| | 1 | 2 | 3 | 4 | 5 | 6 | 7 |
|---|---|---|---|---|---|---|---|
| | Comparative Examples | | | | | | |
| Formation of SWLC | X (not formed) | X | X | X | X | X | X |
| Maintenance of activity (45° C., for 4 weeks) | 9% | 18% | 24% | 24% | 28% | 28% | 32% |
| | Examples | | | | | | |
| Formation of SWLC | ○ (formed) | ○ | ○ | Δ (partially formed) | Δ | Δ | ○ |
| Maintenance of activity (45° C., for 4 weeks) | 82% | 87% | 91% | 42% | 72% | 43% | 65% |

As shown in Table 1, it is understood that retinol can be stabilized and maintain its activity within a SWLC formed by surfactants having 45° C. or higher phase transition temperature together with fatty alcohols and cholesterols.

What is claimed is:

1. An oil-in-water cosmetic composition comprising a retinoid in a cosmetically effective amount and further comprising 0.5~20% by weight of a surfactant having a phase transition temperature of 45° C. or higher, 0.1~10% by weight of fatty alcohol and 0.1~10% by weight of cholesterol, based on a total weight of the composition.

2. The oil-in-water cosmetic composition according to claim 1, wherein said retinoid is one or more selected from the group consisting of retinol, retinal, retinoic acid and its esters and is present in an amount of 100~50,000 IU per 1 g of composition.

3. The oil-in-water cosmetic composition according to claim 1, wherein said surfactant is one or more selected from the group consisting of polyglyceryl(n=2~12) monostearate, polyglyceryl(n=2~12) distearate, polyglyceryl(n=2~12) tristearate, polyglyceryl(n=2~12) tetrastearate, polyglyceryl (n=2~12) pentastearate, polyglyceryl(n=2~12) monopalmitate, polyglyceryl(n=2~12) dipalmitate, polyglyceryl(n=212) tripalmitate, polyglyceryl(n=2~12) tetrapalmitate, polyglyceryl(n=2~12) pentapalmitate, stearyl polyglucose, cetearyl polyglucose, polyglyceryl(n=2~12) alkylglucose monostearate, polyglyceryl(n=2~12) alkylglucose distearate, polyglyceryl(n=2~12) alkylglucose tristearate, polyglyceryl(n=2~12) alkylglucose tetrastearate, polyglyceryl(n=2~12) alkylglucose pentastearate, polyglyceryl(n=2~12) alkylglucose monopalmitate, polyglyceryl(n=2~12) alkylglucose dipalmitate, polyglyceryl(n=2~12) alkylglucose tripalmitate, polyglyceryl(n=2~12) alkylglucose tetrapalmitate, and polyglyceryl(n=2~12) alkylglucose pentapalmitate.

4. The oil-in-water cosmetic composition according to claim 1, wherein said surfactant is one or more selected from the group consisting of polyglyceryl(10) pentastearate-behenyl alcohol-sodium stearyol lactoylate, cetearyl alcohol-cetearyl polyglucose, and polyglyceryl(3)-methylglucose distearate.

5. The oil-in-water cosmetic composition according to claim 1, which further comprises an antioxidant selected from the group consisting of butylated hydroxytoluene and butylated hydroxyanisole and a chelating agent which is ethylenediaminetetraacetic acid.

6. A method for preparing the oil-in-water cosmetic composition according to claim 1 comprising following steps of:

(1) mixing and emulsifying a surfactant, having a phase transition temperature of 45° C. or higher, fatty alcohol and cholesterol in a small portion of distilled water at a temperature of about 70° C., and then adding a retinoid as a core thereto, and then cooling the resulting mixture to room temperature, to yield a liquidcrystal base and an aqueous part;

(2) emulsifying said aqueous part by mixing with the surfactant from (1), and then cooling to room temperature, and then adding water-soluble polymer thereto, to yield a gel-type base; and (3) adding said liquidcrystal base to said gel-type base, and then mixing, to yield an oil-in-water cosmetic composition.

* * * * *